United States Patent [19]

Pálosi et al.

[11] Patent Number: 5,534,644
[45] Date of Patent: Jul. 9, 1996

[54] PROCESS FOR THE PREPARATION OF 4-METHYL-5-(2-CHLOROETHYL)-THIAZOLE AND ANALOGUES THEREOF

[75] Inventors: Endre Pálosi; Dezso Korbonits, both of Budapest; Erzsébet Molnár née Bakó, Szödliget; Ida Szvoboda née Kanzel, Dunakeszi; Gergely Héja, Budapest; Pál Kiss, Budapest; Csaba Gönczi, Budapest; Ferenc Sperber, Budapest; Csaba Huszár, Budapest; György Mihalovics, Budapest; Attila Németh, Göd; Mihály Sü ő, Budapest; Károl Gyüre, Fenyveslitke; István Bóné, Budapest; Ferenc Mórász, Budapest; László Ledniczky, Budapest; Erzsébet Szabó née Kardos, Budapest; Péter Gy ő ri, Budapest; Erzsébet Szalay, Budapest; Károly Bán, Budapest; Iidikó Buttkai, Budapest; Arpád K ő vári, Göd; Sándor Garaczy, Budapest, all of Hungary

[73] Assignee: Aktiebolaget Astra, Sodertalje, Sweden

[21] Appl. No.: 464,308

[22] Filed: Jun. 5, 1995

Related U.S. Application Data

[62] Division of Ser. No. 232,207, filed as PCT/HU92/00042, Oct. 30, 1992 published as WO93/09107 May 13, 1993.

[30] Foreign Application Priority Data

Oct. 30, 1991 [HU] Hungary .................. 34 02/91
Oct. 30, 1991 [HU] Hungary .................. 34 03/91
Oct. 30, 1991 [HU] Hungary .................. 34 04/91
Apr. 3, 1992 [HU] Hungary .................. 11 24/92
Apr. 3, 1992 [HU] Hungary .................. 11 25/92

[51] Int. Cl.⁶ .................. C07C 331/02
[52] U.S. Cl. .................. 558/14; 548/202
[58] Field of Search .................. 558/14

[56] References Cited

PUBLICATIONS

Dudinov, Khim. Geterotsikl. Soedin. (8) 1120–4 (1993).

*Primary Examiner*—Robert Gerstl
*Attorney, Agent, or Firm*—White & Case

[57] ABSTRACT

The present invention relates to a process for the preparation of compounds of general formula (I), wherein R stands for a straight chained $C_{1-5}$ alkyl group substituted by a chlorine atom in the 2-position, and acid addition salts thereof, characterized by reacting a 3,5-dichloro-2-alkanone of general formula (V), wherein R is a defined above, with an inorganic thiocyamate, and a) converting the 3-thiocyanato-5-chloro-2-alkanone of general formula (IV), thus obtained, wherein R is as defined above, into 2-chloro-4-methyl-5-(2-chloroalkyl)-thiazole of general formula (II), wherein R is as defined above, by gaseous hydrochloric acid in an organic solvent, hydrogenating the said compound in the presence of a metal catalyst in an organic solvent, or b) reacting said compound of general formula (IV) with an aqueous mineral acid and treating the 2-hydroxy-4-methyl-5-(2-chloroalkyl)-thiazole of general formula (III), thus obtained with a halogenating agent, and hydrogenating the 2-chloro-4-methyl-5-(2-chloroalkyl)-thiazole of general formula (II) thus obtained, wherein R is as defined above, in an organic solvent in presence of a metal catalyst, and optionally converting the 4-methyl-5-(2-chloroalkyl)-thiazole of general formula (I), wherein R is as defined above, thus obtained or a hydrochloride salt thereof, in a manner known per into another acid addition salt or setting free a compound of general formula (I), wherein R is a defined above, from its acid addition salt.

2 Claims, No Drawings

PROCESS FOR THE PREPARATION OF 4-METHYL-5-(2-CHLOROETHYL)-THIAZOLE AND ANALOGUES THEREOF

This application is a divisional of application Ser. No. 08/232,207, published as WO93/09107 May 13, 1993, which is a 371 of PCT/HU/92/0042 filed Oct. 30, 1992, published as WO93/09107 May 13, 1993.

The invention relates to a novel process for the preparation of 4-methyl-5-(2-chloroalkyl)-thiazoles of the general formula

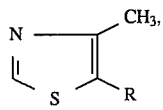 (I)

wherein
R stands for a straight chained $C_{1-5}$alkyl group substituted by a chloride atom in the 2-position,
by the aid of partially known intermediates. The compound of the formula

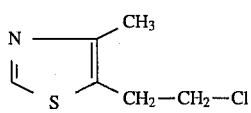 (Ia)

and acid addition salts thereof (Clomethiazole) is the therapeutically widely applied active ingredient of anticonvulsives and sedatives. The compound of the formula (Ia) was first described in 1935 [J. Am. Chem. Soc. 57, 1876 (1935)]. Its hydrochloride and ethane disulphonate salt are disclosed in GB-PS 792,158. Its phosphate salt is known from U.S. Pat. No. 3,639,415.

The known methods for the preparation of the thiazole derivatives unsubstituted in position 2 can be divided into two main types. When proceeding according to methods of the first type the 2-unsubstituted thiazole is obtained in one step. According to methods of the second type thiazole derivatives containing an easily removable substituent in position 2 are prepared and this substituent is removed in a second step.

According to methods of the first type the thiazole ring is formed by reacting a halogenated ketone or aldehyde, which are halogenated in the α-position or aldehyde with thioformamide [Elderfield, R. C.: Heterocyclic Compounds, Vol. 5, page 516 (1957)] (Reaction scheme A).

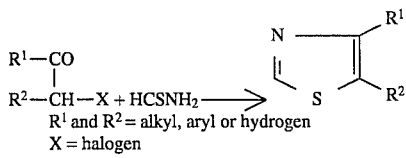
$R^1$ and $R^2$ = alkyl, aryl or hydrogen
X = halogen

This type of methods gives a good yield only in some cases [Buchman and Richardson: J. Am. Chem. Soc. 67, 395 (1945); Erne, Ramirez and Burger: Helv. Chim. Acta 34, 143 (1951)]. A further disadvantage of this method is the difficulty of preparing pure thioformamide and the instable character of thioformamide. To eliminate this difficulty the preparation of thioformamide was carried out in the reaction mixture itself from formamide and phosphorous pentasulphide, but this method succeeded only in some cases [Ganapathi and Venkataraman: Proc. Indian Acad. Sci. 22, 362 (1945)]. This method is strongly contaminating the environment because of the use of phosphorous pentasulphide.

As the direct synthesis described above can hardly be realized on industrial scale, attention was paid to the indirect synthesis variants. One of these variants eliminates the amino group in position 2 via diazotization and the subsequent reduction of the diazonium group [Ganapathi and Venkataraman: Proc. Indian Acad. Sci 22, 366 (1945)]. The 2-amino-thiazole derivative necessary for this method is to be prepared in a separate step from α-halogen-ketone with thiourea [e.g. Tanida, Tamura and Sava: J. Pharm. Soc. Japan 74, 652 (1954); C. A. 48, 10737 (1945)] (reaction scheme B).

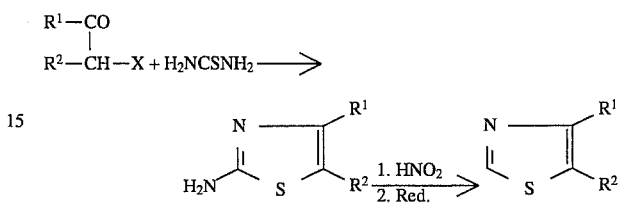

By this route the target compounds can be obtained in poor yields ranging between 30 and 60%.

A further possibility is the oxidative removal of the thio group in position 2 of the thiazole [GB-PS 492,637; Buchman, Reims and Sargnet: J. Org. Chem. 6, 764 (1941)], or the desulphuration of the 2-mercapto-thiazole derivative by boiling with Raney nickel at a great excess [Cook et al: J. Chem. Soc. 1954 (1947); Hurd and Rudner: J. Am. Chem. Soc. 73, 5157 (1951)]. The required 2-mercapto-thiazole has also to be prepared in a separate step from α-halogen-ketone and ammonium-dithiocarbamate (e.g. GB-PS 492,637) (Reaction Scheme C).

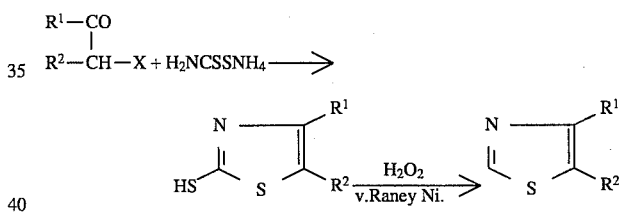

A disadvantage of this method is that for the preparation of ammonium dithiocarbamate carbon disulphide needed, requiring a special workshop when prepared on industrial scale because of the great danger of fire. Further, the reagent and the by-products of the synthesis are contaminating the environment to a great extent. For the desulphuration with Raney nickel a great excess of nickel is required, which significantly increases the costs of the synthesis.

A third possibility is the dehalogenation of the 2-halo-thiazole derivatives. For this purpose mostly zinc is used in an acetic acid medium [GB-PS 456,751; Gibbs and Robinson: J. Chem. Soc. 925 (1945); Andersag and Westphal: Bet. 70, 2035 (1937)].

Catalytic dehalogenation was described only in case of 2-bromo-thiazole-4-carboxylic acid [Erlenmeyer and Morel: Helv. Chim. Acta 25, 1073 (1942)]. The 2-halo-thiazole compounds, i.e. the starting material of the process, are prepared from 2-amino-thiazole derivatives by diazotization and Sandmeyer reaction (e.g. Sara and Maeda: J. Pharm. Soc. Japan 76, 301 (1956); C.A. 50, 13875 (1956)] or from 2-hydroxy-thiazole derivatives with phosphoryl chloride (GB-PS 456,751) or by ring closure of a-thiocyanato-ketones with gaseous hydrochloric acid [Elderfield: Heterocyclic Compounds, Vol. 5, p. 540 (1957)] (Reaction Schemes D

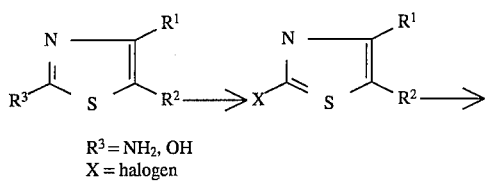

R³ = NH₂, OH
X = halogen

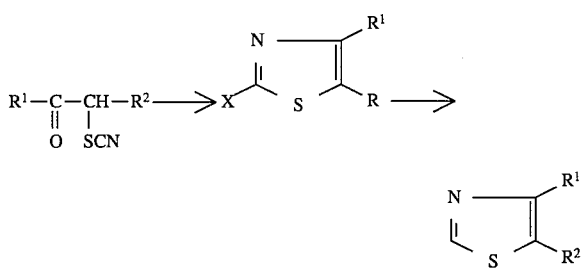

and E).

None of the above methods was used for the preparation of the compounds of the general formula (I) of the present invention, nor for the preparation of the compound of the formula (Ia). The compound of the formula (Ia) was prepared by chlorinating a suitable hydroxy compound with thionyl chloride (FR-PS 3,815 M, GB-PS 792,158 and NL-PA 6,510,389—Reaction Scheme F).

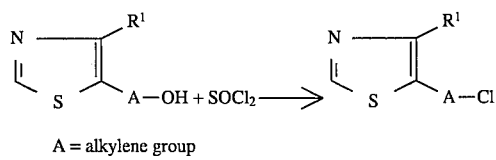

A = alkylene group

In case of Clomethiazole of the formula (Ia) a process was disclosed, according to which a suitable 2-mercapto derivative was oxidized with hydrogen peroxide (CH-PS 200,248).

The 2-chloro-4-methyl-5-(2-chloroethyl)-thiazole of the formula

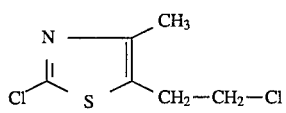

(IIa)

[Acta Pharm. Suec. 8, p. 49 (1982)] and 2-hydroxy- 4-methyl-5-(2-chloroethyl)-thiazole of the formula

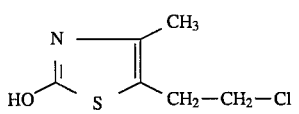

(IIIa)

[Acta Pharm. Suec. 19p. 37 (1982)] are known compounds. None of these compounds, however, has been declared to be a suitable intermediate for the preparation of the compound of the formula (Ia).

In all of the general formulae R is as defined above.

Surprisingly we have found that by reacting a known 3,5-dichloro-2-alkanone of the general formula

(V)

with an inorganic isothiocyanate and converting the 3-thiocyanato-5-chloro-2-alkanone of the general formula

(IV)

thus obtained into 2-chloro-4-methyl-5-(2-chloroalkyl)-thiazole of the general formula

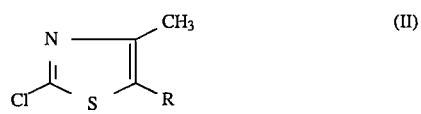

(II)

with gaseous hydrochloric acid in an organic solvent, then hydrogenating the latter in the presence of a metal catalyst in an organic solvent, 4-methyl-5-(2-chloroalkyl)-thiazoles of the general formula (I) are obtained in good yields and high purity by recovering it from the reaction mixture by known methods, preferably in the form of its hydrochloride.

The compounds of the general formula (I) can be converted into acid addition salts by methods known per se. One may also proceed by reacting compounds of the general formula (IV) with an aqueous mineral acid and converting the 2-hydroxy-4-methyl-5-(2-chloroalkyl)-thiazoles of the general formula

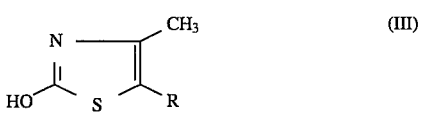

(III)

thus obtained into compounds of the general formula (II) by the aid of a halogenating agent, then by hydrogenating the latter into compounds of the general formula (I) as described above.

Our invention is based on the following recognition: in the compounds of the general formula (V) the reactivity of the chlorine substituent in position α related to the carbonyl group surpasses that of the other chlorine substituent at the end of the chain to such an extent, that exclusively compounds of the general formula (IV) are obtained, the formation of neither dithiocyanato-ketone nor isothiocyanato-ketone can be detected even in traces.

The preparation of the compounds of the general formula (II) containing a thiazole ring from the compounds of the general formula (IV) is not obvious in the knowledge of the literature.

The removal of the chlorine substituent on the thiazole ring from the dichloro compounds of the general formula (II) by selective hydrogenation is surprising and not obvious, since the inactivity of the chlorine substituent at the end of the chain could not be expected by a person skilled in the art.

The conversion of the compounds of the general formula (IV) into 2-hydroxy-thiazole derivatives of the general formula (III) preferably in the presence of phosphoric acid, further the halogenation of the compounds of the general formula (III) with a slight excess of the halogenating agent and in the most suitable solvent is accompanied with significant technological and environmental advantages.

The method described in the examples of the present invention is novel and represents an alternative synthesis route which cannot be derived from the known preparation methods of the Clomethiazole of the formula (Ia).

In the following an advantageous embodiment of the process of our invention is presented on the synthesis of the compound of the formula (Ia).

A compound of the formula

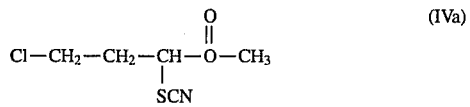

is prepared from a known compound of the formula

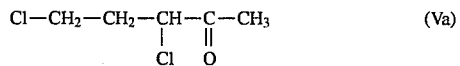

[Acta Chem. Hung. 3, 157 (1953)] in water, in an organic solvent or in a mixture of water and an organic solvent, by the aid of inorganic thiocyanates, preferably sodium, potassium or ammonium thiocyanate. Most preferably an organic solvent, e.g. acetone, methyl-ethyl-ketone, ethyl acetate, butyl acetate, methanol, ethanol, isopropyl acetate or ethyl propionate, is used.

The reaction may be carried out at a temperature ranging from 20° to 100° C., preferably at the boiling point of the solvent, with an equivalent amount or with a slight (1 to 5 mol %) excess of the inorganic rhodanide.

The dichloro derivative of the general formula (IIa) is obtained by reacting a compound of the formula (IVa), dissolved in an organic solvent, with anhydrous gaseous hydrochloric acid. As a solvent most preferably water-immiscible ethers and esters, which do not dissolve water, e.g. ethylacetate, butyl acetate or diisopropylether are used. Lower aliphatic alcohols may preferably be used, e.g. methanol, ethanol, n-propanol, isopropanol or butanol, lower fatty acids, e.g. acetic acid or propionic acid, or halogenated hydrocarbons, e.g. carbontetrachloride, chloroform or 1,2-dichloroethane may also be preferred.

The reaction is carried out at a temperature ranging from 0° to 100° C., preferably from 0° to 40° C.

The selective hydrogenation of the compound of the formula (IIa) is carried out in the presence of a metal catalyst in an organic solvent.

The metal catalyst is preferably palladium on active charcoal or palladium containing selenium (Examples 1, 3 and 5 of published PCT-application No. 89/2429) and a catalyst containing rhodium or ruthenium may also be applied.

As an organic solvent lower aliphatic alcohols, e.g. methanol, ethanol, n-propanol or isopropanol, lower esters of aliphatic carboxylic acids, e.g. ethyl acetate, butyl acetate, methyl acetate, isopropyl acetate or ethylpropionate, aromatic hydrocarbons, e.g. benzene or toluene, or open-chained ethers, e.g. cellosolve, methylcellosolve, butylcellosolve, dimethylcellosolve or diglyme) can be used.

Hydrogenation may be carried out at atmospheric pressure or at a slight overpressure (0.05–0.7 MPa).

The splitting hydrochloric acid is bound by the forming thiazole derivative of the formula (Ia), then it can also be recovered in the form of a hydrochloride of the formula (Ia).

During hydrogenation as an acid binding agent alkali hydroxides, e.g. sodium or potassium hydroxide, or organic bases, e.g. triethylamine, may be applied, then the basic compound of the formula (Ia) itself is obtained.

In the preparation of the compound of the formula (IIIa) α-thiocyanato-ketone of the formula (IVa) is treated by aqueous phosphoric acid, in this case no organic solvent is needed and no corrosion problem arises as opposed to the known acetic acid—concentrated sulfuric acid or acetic acid—concentrated hydrochloric acid reagents. Further, no environmentally damaging by-products are formed during the processing of the reaction mixture.

The reaction is carried out at a temperature ranging from 50° to 120° C., preferably from 90° to 100° C.

When halogenating the compounds of the formula (IIIa) preferably phosphorus halides, e.g. phosphoryl chloride, phosphorus pentachloride or phosphorus trichloride are used as halogenating agent.

As an organic solvent preferably halogenated aliphatic hydrocarbons, e.g. 1,2-dichloroethane, 1,1,2-trichloroethane, trichloroethylene or 1,1,2,2-tetrachloroethane, aromatic hydrocarbons, e.g. benzene, toluene or xylene, specially preferably halogenated aromatic hydrocarbons, e.g. chlorobenzene, 1,2-dichlorobenzene or 1,2,4-trichlorobenzene may be used.

The reaction is carried out at a temperature ranging from 80° to 150° C., preferably from 100° to 140° C.

The other compounds of the general formulae (I), (II), (III) and (IV) can preferably be prepared by the methods described above.

The preparation of the compounds of the general formula (V) is disclosed in the examples where no literature reference is available.

The present invention is elucidated in more detail in the following non-limiting examples.

EXAMPLE 1

77.8 g (0.5 moles) of 3,5-dichloro-2-pentanone [prepared according to Acta Chim. Hung. 3, 157 (1953)] are added to the solution of 49.9 g (0.513 moles) of potassium rhodanide in 500 ml of acetone. The solution is boiled under stirring for 4 hours. The reaction mixture is cooled to room temperature and the precipitated potassium chloride is filtered off and washed with acetone. The filtrate is evaporated, the residue is dissolved in benzene and the benzene solution is washed 3 times with water. After drying with sodium sulphate, the benzene is distilled off. 62.2 g (93%) of 3-thiocyanato-5-chloro-2-pentanone are obtained in the form of a red oil. After distilling at a lower pressure a faint yellow oil is obtained, its boiling point is 112° C. at a pressure of 26.6 Pa, $n_D^{20}=1.5110$. According to infrared spectrum it does not contain any isothiocyanate.

Analysis for the formula $C_6H_8ClNOS$: calculated: C%=40.56, H%=4.53, N%=7.88, Cl%=19.95, S%=18.04; found: C%=41.25, H%=4.59, N%=8.13, Cl%=20.32, S%=17.90;

The NMR data support the structure.

EXAMPLE 2

A solution of 155.5 g (1 mole) of 3,5-dichloro-2-pentanone with 83 g (1.024 moles) of sodium rhodanide in 1 liter of methyl-ethyl-ketone is boiled for 1 hour under stirring. Then the procedure described in Example 1 is followed. 171 g (96.2%) of 3-thiocyanato-5-chloro-2-pentanone are obtained, which after distillation identical in all respect with the product of Example 1.

EXAMPLE 3

A suspension of 7.8 g (0.05 moles) of 3,5-dichloro-2-pentanone with 3.9 g (0.051 moles) of ammonium rhodanide in 50 cm³ of methyl-ethyl-ketone is boiled for 1 hour under stirring. Then the procedure described in Example 1 is followed. 8.5 g (95.5%) of 3-thiocyanato-5-chloro-2-pentanone are obtained, which after distillation is identical in all respect with the product of Example 1.

EXAMPLE 4

A solution of 7.8 g (0.05 moles) of 3,5-dichloro-2-pentanone with 4.15 g (0.051 moles) of sodium rhodanide in 50 cm³ of ethanol is boiled for 2 hours under stirring. Then the procedure described in Example 1 is followed. 7.7 g (87%) of 3-thiocyanato-5-chloro-2-pentanone are obtained, which is identical in all respect with the product of Example 1 after distillation.

EXAMPLE 5

To a solution of 4.86 g (0.05 moles) of potassium rhodanide in 10 cm³ of water 7.8 g (0.05 moles) of 3,5-dichloro-2-pentanone are added and the reaction mixture is stirred for 3 hours at a temperature of 80° C. After cooling the precipitating oil is separated and the aqueous phase is shaken twice with 20 cm³ of benzene each. The separated oil is combined with the benzene solution, washed with water and dried over sodium sulfate. After filtering and evaporating 7.4 g (83.5%) of 3-thiocyanato-5-chloro-2-pentanone are obtained, which after distillation is identical in all respect with the product of Example 1.

EXAMPLE 6

A solution of 17.7 g (0.1 mole) of 3-thiocyanato-5-chloro-pentanone-2 in 170 cm³ of anhydrous ethylacetate is saturated with gaseous hydrochloric acid. The temperature of the reaction mixture is kept below 10° C. by ice-cooling. The solution obtained is let to stand overnight at room temperature. The next day the solution is poured onto ice and its pH-value is adjusted to a value between 6 and 7 with a 20% sodium hydroxide solution. The phases are separated and the aqueous phase is shaken with 150 ml of ethyl acetate. The combined ethyl acetate solutions are washed neutral with water and a 5% sodium hydrogen carbonate solution and dried over sodium sulphate. After distilling off the solvent, the residue is distilled under reduced pressure to obtain 14.8 g (75.5%) of 2-chloro-4-methyl-5-(2-chloroethyl)-thiazole in the form of a faint yellow oil. The boiling point is 104° C. at a pressure of 40 Pa, $n_D^{20}$=1.5505.

Analysis for the formula $C_6H_7Cl_2NS$: calculated: C%=36.70, H%=3,39, N%=7.14, Cl%=36.15, S%=16.35; found: C%=37.01, H%=3.71, N%=7.48, Cl%=35.40, S%=15.97.

The IR and NMR data support the structure. The content of the product is more than 95% determined by gas chromatography.

EXAMPLE 7

25 g (0,14 moles) of 3-thiocyanato-5-chloro-pentanone-2 are dissolved in 170 cm³ of butyl acetate saturated with gaseous hydrochloric acid at 0° C. Into the reaction mixture gaseous hydrochloric acid is introduced until saturation under cooling with ice, keeping the temperature below 10° C. After saturation the reaction mixture is stirred for further 20 minutes under cooling, then the temperature is slowly increased to 40° C. The reaction mixture is stirred at this temperature for 20 minutes and after cooling to room temperature it is poured onto ice. The pH-value of the mixture is adjusted between 7 and 8 by adding a 40% sodium hydroxide solution. The mixture is processed further as described in Example 6.

20.8 g (76%) of 2-chloro-4-methyl-5-(2-chloroethyl)-thiazole are obtained, which is identical in every respect with the product obtained in Example 6.

EXAMPLE 8

One proceeds as described in Example 7 with the difference that instead of butyl acetate abs. ethanol is used. After the termination of the reaction the reaction mixture is evaporated in vacuo and to the residue water and 20% sodium hydroxide solution are added to a pH-value of 7. Furtheron one proceeds as described in Example 7. 17 g (62%) of 2-chloro-4-methyl-5-(2-chloroethyl)-thiazole are obtained which is identical in every respect with the product obtained in Example 6.

EXAMPLE 9

One proceeds as described in Example 6 with the difference that instead of ethyl acetate diisopropylether is used. 14 g (74%) of 2-chloro-4-methyl-5-(2-chloroethyl)-thiazole are obtained which is identical in every respect with the product obtained in Example 6.

EXAMPLE 10

One proceeds as described in Example 8 with the difference that instead of abs. ethanol glacial acetic acid is used. 20.2 g (73.5%) of 2-chloro-4-methyl-5-(2-chloroethyl)-thiazole are obtained, which is identical in every respect with the product obtained in Example 6.

EXAMPLE 11

One proceeds as described in Example 6 with the difference that instead of ethyl acetate carbon tetrachloride is used. 12 g (61%) of 2-chloro-4-methyl-5-(2-chloroethyl)-thiazole are obtained, which is identical in every respect with the product obtained in Example 6.

EXAMPLE 12

355,3 g (2 moles) of distilled 3-thiocyanato-5-chloro-2-pentanone are added into 360 cm³ of 85% phosphoric acid under stirring. The temperature of the reaction mixture is increased to 95° C. in water bath within about 1 hour and then it is stirred for half and hour between 95° to 100° C. The brown solution is cooled to 20° C. and poured into 660 cm³ of water. The precipitated beige crystals are removed by suction after a stirring for half an hour, washed neutral with water and dried in vacuo at a temperature of 60° C. 337 g (95%) of pale beige 2-hydroxy-4-methyl-5-(2-chloroethyl)-thiazole are obtained, m.p.: 151°–152° C. After recrystallization from benzene the melting point is 157°–158° C.

Analysis as calculated for C6H8ClNOS: calculated: C%=40.56, H%=4.53, N%=7.88, S%=18.04, Cl%=19.95; found: C%=40.74, H%=4.52, N%=7.57, S%=17.94, Cl%=19.68.

The structure of the compound is confirmed also by the IR and NMR data.

EXAMPLE 13

One proceeds as described in Example 12 using non-distilled 3-thiocyanato-5-chloro-2-pentanone content: 80%, determined by gas chromatography). 234 g (66%) of 2-hydroxy-4-methyl-5-(2-chloroethyl)-thiazole are obtained, which melts at 141° to 146° C.

EXAMPLE 14

A suspension of 177.6 g (1 mole) of 2-hydroxy-4-methyl-5-(2-chloroethyl)-thiazole in 530 cm³ of anhydrous chlorobenzene is heated to 100° C. under stirring. 306.6 g (2 moles) of phosphoryl chloride are flown into the solution in 30 minutes, then it is stirred at a temperature of 125°–130° C. until the formation of hydrogen chloride ceases (about 2 hours). The reaction mixture is cooled to 20° C., then it is poured onto 1.5 kg of ice. The phases are separated, the aqueous phase is extracted twice with 200 cm³ of chlorobenzene each. The combined phases containing the chlorobenzene are washed acid-free with water and then with a 5% sodium hydrogen carbonate solution and then evaporated under reduced pressure. The brown residue is fractionated in vacuo. 145 g (74%) of 2-chloro-4-methyl-5-(2-chloroethyl)-thiazole are obtained. The boiling point is 102° C. at a pressure of 53.2 Pa, $n^{20}_D$=1.5512, $n^{30}_D$=1.5468

Purity: 99.4% (by gas chromatography).

Analysis as calculated for $C_6H_7Cl_2NS$: calculated: C%=36.70, H%=3.59, N%=7.14, Cl%=36.15, S%=16.35; found: C%=36.98, H%=3.68, N%=7.28, Cl%=35.70, S%=16.05.

The structure of the compound is confirmed also by the IR and NMR data.

EXAMPLE 15

To a solution of 63 g (0.32 moles) of 2-chloro-4-methyl-5-(2-chloroethyl)-thiazole in 630 cm³ of a 96% ethanol 9 g of a wet palladium on charcoal catalyst (palladium content: 8%) are added. The mixture is hydrogenated at atmospheric pressure. The termination of the reaction is indicated by the cease of the hydrogen consumption. After filtering off the catalyst the solution is evaporated, the residue is dissolved in water and the solution is neutralized with sodium hydrogen carbonate (pH 7). The separated oil is shaken out with chloroform. The residue after the evaporation of the chloroform solution is distilled under reduced pressure. 47 g (91%) of 4-methyl-5-(2-chloroethyl)-thiazole are obtained. Its boiling point is 105° C. at a pressure of 0.93 KPa, $n_D^{20}$=1.5430. Its active agent content is 98.8%, determined by gas chromatography.

The infrared and NMR spectra of the product is identical with that of the authentic sample.

EXAMPLE 16

One proceeds as described in Example 15 with the difference that the hydrogenation is carried out at a pressure of 0.3 MPa.

46.5 g (90%) of 4-methyl-5-(2-chloroethyl)-thiazole are obtained which is identical in every respect with the product obtained in Example 15.

EXAMPLE 17

One proceeds as described in Example 15 with the difference that instead of ethanol methanol is used.

42.9 g (83%) of 4-methyl-5-(2-chloroethyl)-thiazole are obtained which is identical in every respect with the product obtained in Example 15.

EXAMPLE 18

One proceeds as described in Example 15 with the difference that after evaporation the residual solid substance is separated.

61.5 g (97%) of 4-methyl-5-(2-chloroethyl)-thiazole hydrochloride are obtained. Its melting point after recrystallization from anhydrous ethanol is 136°–137° C.

Analysis as calculated for $C_6H_9Cl_2NS$: calculated: C%=36.37, H%=4.58, N%=7.07, Cl%=35.79; found: C%=36.18, H%=4.52, N%=7.10, Cl%=35.89.

EXAMPLE 19

One proceeds as described in Example 15 with the difference that acetone is added to the solution obtained after filtering off the catalyst and the precipitating solid substance is filtered.

59.4 g (93.7%) of 4-methyl-5-(2-chloroethyl)-thiazole hydrochloride are obtained. Its melting point is 137°–137.5° C. after recrystallized in anhydrous ethanol.

Analysis as calculated for $C_6H_9Cl_2NS$: calculated: C%=36.37, H%=3.59, N%=4.58, Cl%=35.79; found: C%=36.17, H%=4.51, N%=7.12, Cl%=35.89.

EXAMPLE 20

One proceeds as described in Example 15 with the difference that as catalyst 9 g of palladium on charcoal containing selenium are added. This catalyst has been prepared according to Example 5 of the PCT-application published under No. WO-89/02429 (page 12).

46.2 g (89.4%) Of 4-methyl-5-(2-chloroethyl)-thiazole are obtained which is identical with the product obtained in Example 15 in respect of its physical constants and active agent content.

EXAMPLE 21

83 g (1.024 moles) of sodium rhodanide are added to a solution of 155.5 g (1 mole) of 3,5-dichloro-2-pentanone in 1 liter of butyl acetate. The suspension is stirred for 4 hours in hot water bath. After cooling the sodium chloride formed is filtered off and the filtrate is washed 3 times with water. After drying over sodium sulfate the butyl acetate is distilled off.

168 g (94%) of 3-thiocyanato-5-chloro-2-pentanone are obtained in the form of red oil. After distillation this product is identical with the product obtained in Example 1.

EXAMPLE 22

83 g (1.024 moles) of sodium rhodanide are added to a solution of 155.5 g (1 mole) of 3,5-dichloro-2-pentanone in 1 liter of butyl acetate. The suspension is stirred for 4 hours in hot water bath. After cooling the sodium chloride formed is filtered off and the filtrate is washed 3 times with water and dried over sodium sulfate. After filtering off the drying agent the light red-brown filtrate is cooled under 10° C. by icy water and saturated with gaseous hydrochloric acid under stirring, keeping the temperature under 10° C. After saturation the reaction mixture is stirred for further 20 minutes under cooling, then the temperature is increased slowly to 40° C. The reaction mixture is stirred at this temperature for 20 minutes and poured onto ice after cooling down to room temperature. The phases are separated, the aqueous phase is shaken with 150 cm³ of butyl acetate. The combined butyl acetate solutions are washed neutral with water and 5% sodium hydrogen carbonate solution, then dried over sodium sulfate. After distilling off the solvent the residue is distilled off under reduced pressure to obtain 121 g (66%) of 2-chloro-4-methyl-5-(2-chloroethyl)-thiazole in the form of pale yellow oil, which is identical in every respect with the product obtained in Example 1.

EXAMPLE 23

One proceeds as described in Example 1 by using 8.45 g (0.05 moles) of 3,5-dichloro-2-hexanone, 5 g of potassium rhodanide and 50 cm³ of acetone.

8.9 g (93%) of 3-thiocyanato-5-chloro-2-hexanone are obtained. After distillation under reduced pressure it is a pale yellow oil, its boiling point is 107°–108° C. at a pressure of 53.3 Pa, $n_D^{20}$=1.5050.

According to the IR spectrum data the product contains no isothiocyanate.

Analysis as calculated for $C_7H_{10}ClNOS$: calculated: C%=43.82, H%=5.25, N%=7.30, Cl%=18.50, S%=16.72; found: C%=43.57, H%=5.96, N%=7.61, Cl%=18.36. S%=16.58.

EXAMPLE 24

One proceeds as described in Example 1 by using 18.3 g (0.1 mole) of 3,5-dichloro-2-heptanone, 10 g (0.102 moles) of potassium rhodanide and 100 cm³ of acetone.

19.1 g (93%) of 3-thiocyanato-5-chloro-2-heptanone are obtained. After distillation under reduced pressure it is a pale yellow oil, its boiling point is 124° C. at a pressure of 53.3 Pa, $n_D^{20}$=1.4983.

According the IR spectrum data the product contains no isothiocyanate.

Analysis as calculated for $C_8H_{12}ClNOS$: calculated: C%=46.70, H%=5.88, N%=6.80, Cl%=17.23, S%=15.58; found: C%=46.93, H%=5.69, N%=6.68, Cl%=16.87. S%=13.37.

EXAMPLE 25

One proceeds as described in Example 7 by using 9.6 g (0.05 moles) of 3-thiocyanato-5-chloro-2-hexanone and 55 cm³ of butyl acetate.

7.7 g (80%) of 2-chloro-4-methyl-5-(2-chloropropyl)-thiazole are obtained in the form of a colourless liquid. Its boiling point is 96° C. at a pressure of 66.6 Pa, $n_D^{20}$=1.5400.

Analysis as calculated for $C_7H_9Cl_2NS$: calculated: C%=40.00, H%=4.31, N%=6.66, Cl%=33.74, S%=15.26; found: C%=39.75, H%=4.24, N%=6.70, Cl%=33.68. S%=14.82.

The structure of the compound is confirmed by the IR and NMR data.

EXAMPLE 26

One proceeds as described in Example 7 by using 10.25 g (0.05 moles) of 3-thiocyanato-5-chloro-2-heptanone and 55 cm³ of butyl acetate.

8.9 g (79.5%) of 2-chloro-4-methyl-5-(2-chlorobutyl)-thiazole are obtained in the form of a colourless liquid. Its boiling point is 108° C. at a pressure of 53.2 Pa, $n_D^{20}$=1.5263.

Analysis as calculated for $C_8H_{11}Cl_2NS$: calculated: C%=42.86, H%=4.94, N%=6.28, Cl%=31.63, S%=14.30; found: C%=43.07, H%=4.79, N%=6.13, Cl%=31.33. S%=14.20.

The structure of the compound is confirmed by the IR and NMR data.

EXAMPLE 27

One proceeds as described in Example 15 by using 7 g (0.033 moles) of 2-chloro-4-methyl-5-(2-chloro-propyl)-thiazole, 60 cm³ of 96% ethanol and 1 g of wet palladium on charcoal catalyst (palladium content: 8%).

5 g (86%) of 4-methyl-5-(2-chloropropyl)-thiazole are obtained in the form of a colourless liquid. Its boiling point is 78° C. at a pressure of 40 Pa, $n_D^{20}$=1.5330.

Analysis as calculated for $C_7H_{10}ClNS$: calculated: C%=47.30, H%=5.73, N%=7.97, Cl%=20.17, S%=18.24; found: C%=47.53, H%=5.25, N%=7.63, Cl%=20.46. S%=18.18.

The structure of the compound is confirmed by the IR and NMR data.

EXAMPLE 28

One proceeds as described in Example 15 by using 5.3 g (0.024 moles) of 2-chloro-4-methyl-5-(2-chlorobutyl)-thiazole, 50 cm³ of 96% ethanol and 0.9 g of wet palladium on charcoal catalyst .(palladium content: 8%).

3.7 g (81%) of 4-methyl-5-(2-chlorobutyl)-thiazole are obtained in the form of a colourless liquid. Its boiling point is 94° C. at a pressure of 66.5 Pa, $n_D^{20}$=1.5263.

Analysis as calculated for $C_8H_{12}ClNS$: calculated: C%=50.64, H%=6.37, N%=7.38, Cl%=18.69, S%=16.90; found: C%=49.98, H%=6.21, N%=7.12, Cl%=18.20. S%=17.08.

The structure of the compound is confirmed by the IR and NMR data.

EXAMPLE 29

One proceeds as described in Example 12 by using 15.3 g (0.05 moles) of 3-thiocyanato-5-chloro-2-hexanone and 16 cm³ of 83% phosphoric acid.

11.2 g (73%) of 2-hydroxy-4-methyl-5- (2-chloro-propyl)-thiazole are obtained, which melts at 91°–93° C.

Analysis as calculated for $C_7H_{10}ClNOS$: calculated: C%=43.85, H%=5.25, N%=7.30, Cl%=18.49, S%=16.72; found: C%=43.52, H%=5.12, N%=7.05, Cl%=18.50. S%=16.82.

The structure of the compound is confirmed by the IR and NMR data.

EXAMPLE 30

One proceeds as described in Example 12 by using 13.3 g (0.064 moles) of 3-thiocyanato-5-chloro-2-heptanone and 14 cm³ of 85% phosphoric acid.

9.5 g (71.5%) of 2-hydroxy-4-methyl-5-(2-chloro-butyl)-thiazole are obtained, which melts at 84°–85° C.

Analysis as calculated for $C_8H_{12}ClNOS$: calculated: C%=46.70, H%=5.88, N%=6.80, Cl%=17.23, S%=15.58; found: C%=46.04, H%=5.61, N%=6.20 Cl%=16.98 S%=15.30.

The structure of the compound is confirmed by the IR and NMR data.

EXAMPLE 31

One proceeds as described in Example 14 by using 9.7 g (0.05 moles) of 2-hydroxy-4-methyl-5-(2-chloro-propyl)-thiazole, 15,3 g (0.1 mole) of phosphoryl chloride and 26 cm³ of anhydrous chlorobenzene.

8.4 g (83.3%) of.2-chloro-4-methyl-5-(2-chloro-propyl)-thiazole are obtained in the form of a colourless oil. Its boiling point is 102° C. at a pressure of 80 Pa, $n_D^{20}$=1.5400.

Analysis as calculated for $C_7H_9C_{12}NS$: calculated: C%=40.00, H%=4.31, N%=6.66, Cl%=33.74, S%115.26; found: C%=39.85, H%=4.35, N%=6.76, Cl%=33.65. S%=14.95.

The structure of the compound is confirmed by the IR and NMR data.

EXAMPLE 32

One proceeds as described in Example 14 by using 7.4 g (0.036 moles) of 2-hydroxy-4-methyl-5-(2-chlorobutyl)-thiazole, 11 g (0,072 moles) of phosphoryl chloride and 19 cm³ of anhydrous chlorobenzene.

6.7 g (83.3%) of 2-chloro-4-methyl-5-(2-chlorobutyl)-thiazole are obtained in the form of a colourless oil. Its boiling point is 108° C. at a pressure of 53.2 Pa, $n_D^{20}$=1.5352.

Analysis as calculated for $C_8H_{11}Cl_2NS$: calculated: C%=42.86, H%=4.94, N%=6.28, Cl%=31.63, S%=14.30; found: C%=42.98, H%=4 81, N%=6.21, Cl%=31.44, S%=14.20.

The structure of the compound is confirmed by the IR and NMR data.

Preparation of further starting materials

EXAMPLE 1

3,5-dichloro-hexanone

A mixture of 17.7 g (0.1 mole) of α-chloro-α-aceto-δ-valerolactone [prepared according to J. Am. Chem. Soc. 67, 398 (1945)] and 35 cm³ of abs. hydrochloric acid is heated slowly to 90° C. under stirring and is stirred at this temperature until the gas formation stops. After cooling the dark solution is poured into 100 cm³ of water, the separating oil is extracted with chloroform. The chloroform containing solution is washed by 50 cm³ of 5% sodium hydrogen carbonate solution. After evaporation the residual oil is distilled in vacuo. 5 g (30%) of 3,5-dichloro-2-hexanone are obtained in the form a colourless liquid. The boiling point is 38° C. at a pressure of 26.6 Pa.

Analysis as calculated for $C_6H_{10}Cl_2O$: calculated: C%=42.62, H%=5.96, Cl%=41.94; found: C%=42.77, H%=5.76, Cl%=41.50.

The structure of the compound is confirmed by the IR and NMR data.

EXAMPLE 2

3,5-Dichloro-2-heptanone a) α-Chloro-α-acetyl-δ-ethyl-δ-butyrolactone

Into a solution of 58.2 g (0.37 moles) of α-acetyl-δ-ethyl-δ-butyrolactone [prepared according to J. Pharm. Sci. 52, 733 (1963)] in 60 cm³ benzene 50 g of (0.37 moles) of sulphuryl chloride are added dropwise under stirring and cooling in 2 hours, keeping the temperature of the reaction mixture between 5° and 10° C. After completing the addition the reaction mixture is let to warm to room temperature and stirred at this temperature until the gas formation ceases. Then it is poured into 400 cm³ of water, the phases are separated and the water is extracted with 200 cm³ of benzene. The benzene containing solution is washed with 100 cm³ of 5% sodium hydrogencarbonate solution. After evaporation the residual oil is distilled in vacuo. The title compound is obtained in the form of a colourless liquid in an amount of 58.9 g (82.5%), its boiling point is 91° C. at a pressure of 80 Pa, $n_D^{20}$=1,4623.

Analysis as calculated for $C_8H_{11}ClO_3$: calculated: C%=50.40, H%=5.81, Cl%=18.60; found: C%=50.63, H%=5.55, Cl%=18.84.

b) 3,5-dichloro-2-heptanone

The title compound is prepared according to the method described in Example 1 starting from 49 g (0.26 moles) of α-chloro-α-acetyl-δ-ethyl-δ-butyrolactone and 98 cm³ of abs. hydrochloric acid. After distillation 22 g (47%) of the title compound is obtained. Its boiling point is 68°–70° C. at a pressure of 133.3 Pa, $n_D^{20}$=1,4600.

Analysis as calculated for $C_7H_{12}C_{12}O$: calculated: C%=45.91, H%=6.60, Cl%=38.73; found: C%=45.66, H%=6.55, Cl%=38.90.

We claim:

1. A compound of the general formula

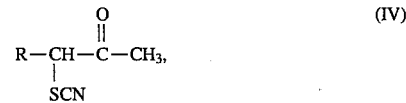

(a 3-thiocyanato-5-chloro-2-alkanone) wherein R is defined as a straight chain C1–C5 alkyl group substituted by a chlorine in the 2-position.

2. A compound according to claim 1 wherein R stands for 2-chloroethyl.